United States Patent
Sakaida et al.

(10) Patent No.: US 10,744,159 B2
(45) Date of Patent: Aug. 18, 2020

(54) METHOD FOR EVALUATING MESENCHYMAL STEM CELL ACTIVITY, METHOD FOR CULTURING MESENCHYMAL STEM CELLS, METHOD FOR PRODUCING THERAPEUTIC AGENT FOR LIVER DYSFUNCTION, AND THERAPEUTIC AGENT FOR LIVER DYSFUNCTION

(71) Applicants: SHIBUYA CORPORATION, Kanazawa-shi, Ishikawa (JP); YAMAGUCHI UNIVERSITY, Yamaguchi-shi, Yamaguchi (JP)

(72) Inventors: Isao Sakaida, Ube (JP); Shuji Terai, Niigata (JP); Taro Takami, Ube (JP); Koichi Fujisawa, Ube (JP); Naoki Yamamoto, Ube (JP); Kenji Yoneda, Kanazawa (JP)

(73) Assignees: YAMAGUCHI UNIVERSITY, Yamaguchi-shi, Yamaguchi (JP); SHIBUYA CORPORATION, Kanazawa-shi, Ishikawa ( * ) Notice: Subject to any disclaimer, the term of this patent is extended or adjusted under 35 U.S.C. 154(b) by 375 days.

(21) Appl. No.: 15/512,390

(22) PCT Filed: Aug. 19, 2015

(86) PCT No.: PCT/JP2015/073198
§ 371 (c)(1),
(2) Date: Mar. 17, 2017

(87) PCT Pub. No.: WO2016/042965
PCT Pub. Date: Mar. 24, 2016

(65) Prior Publication Data
US 2017/0246211 A1    Aug. 31, 2017

(30) Foreign Application Priority Data
Sep. 17, 2014  (JP) .................. 2014-189378

(51) Int. Cl.
*A61K 35/28* (2015.01)
*C12Q 1/48* (2006.01)
(Continued)

(52) U.S. Cl.
CPC .............. *A61K 35/28* (2013.01); *A61K 35/12* (2013.01); *A61K 45/00* (2013.01); *C12N 5/0663* (2013.01);
(Continued)

(58) Field of Classification Search
None
See application file for complete search history.

(56) References Cited

U.S. PATENT DOCUMENTS 8,039,256 B2  10/2011  Sakai et al.
2011/0076770 A1  3/2011  Sakai et al.

FOREIGN PATENT DOCUMENTS

JP  2011-67175 A  4/2011

OTHER PUBLICATIONS

En-Hui, Wu; et al; "Effect of hypoxia on the gene profile of human bone marrow-derived mesenchymal stem cells" Acta Physiologica Sinica, 59, 227-232, 2007 (Year: 2007).*
Dzeja, Petras; Terzic, Andre; "Adenylate Kinase and AMP Signaling Networks: Metabolic Monitoring, Signal Communication and Body Energy Sensing " International Journal of Molecular Sciences, 10, 1729-1772, 2009 (Year: 2009).*
(Continued)

*Primary Examiner* — David W Berke-Schlessel
(74) *Attorney, Agent, or Firm* — Flynn Thiel, P.C.

(57) ABSTRACT

A method for evaluating the activity level of mesenchymal stem cells, and a method for culturing mesenchymal stem cells using the evaluation method in the field of culturing mesenchymal stem cells for regenerative medicine, and further, a method for producing a therapeutic agent for liver
(Continued)

dysfunction and a therapeutic agent for liver dysfunction. This method for evaluating mesenchymal stem cell activity has an assay step for assaying the amount of adenylate kinase 4 (AK4) in the mesenchymal stem cells; and a determination step for determining the activity level of the mesenchymal stem cells from the assayed amount of adenylate kinase 4.

7 Claims, 2 Drawing Sheets

(51) Int. Cl.
- *C12N 5/0775* (2010.01)
- *G01N 33/50* (2006.01)
- *A61K 45/00* (2006.01)
- *C12Q 1/04* (2006.01)
- *A61K 35/12* (2015.01)

(52) U.S. Cl.
CPC ............... *C12Q 1/04* (2013.01); *C12Q 1/48* (2013.01); *C12Q 1/485* (2013.01); *C12Y 207/04003* (2013.01); *G01N 33/5005* (2013.01); *C12N 2503/00* (2013.01); *G01N 2333/91235* (2013.01)

(56) References Cited

OTHER PUBLICATIONS

Notification of Transmittal of International Search Report issued in Application No. PCT/JP2015/073198 dated Nov. 17, 2015 (2 pages).
International Search Report with English translation issued in Application No. PCT/JP2015/073198 dated Nov. 17, 2015 (5 pages).
Written Opinion of International Searching Authority issued in Application No. PCT/JP2015/073198 dated Nov. 17, 2015 (3 pages).
Quintanilha, Luiz Fernando et al., Canine mesenchymal stem cells show antioxidant properties against thioacetamide-induced liver injury in vitro and in vivo, Hepatology Research, Aug. 19, 2013, 44, pp. E206-217.
Roszek, K., et al., Nucleotides metabolizing ectoenzymes as possible markers of mesenchymal stem cell osteogenic differentiation, Biochem. Cell Biol., 2013, 91(3), pp. 176-181.
Yamashiro, Y., et al., Expression of mRNAs encoding adenylate kinase isozymes 1, 2, 3, and 4 in mouse tissues and during neuronal differentiation of P19 embryonal carcinoma cells, Bull. Yamaguchi Med. Sch., 2001, 47(3-4), pp. 55-68.
Noma, T., et al., Structure and expression of human mitochondrial adenylate kinase targeted to the mitochondrial matrix, Biochem. J., 2001, 358, pp. 225-232.
Miyoshi, K., et al., Localization of Adenylate Kinase 4 in Mouse Tissues, ACTA Histochemica Et Cytochemica, 2009, 42(2), pp. 55-64.

* cited by examiner

METHOD FOR EVALUATING MESENCHYMAL STEM CELL ACTIVITY, METHOD FOR CULTURING MESENCHYMAL STEM CELLS, METHOD FOR PRODUCING THERAPEUTIC AGENT FOR LIVER DYSFUNCTION, AND THERAPEUTIC AGENT FOR LIVER DYSFUNCTION

TECHNICAL FIELD

The present invention relates to the field of culturing mesenchymal stem cells for regenerative medicine and, more specifically, to a method for evaluating the activity level of mesenchymal stem cells, and a method for culturing mesenchymal stem cells using the evaluation method, and further to a method for producing a therapeutic agent for liver dysfunction and a therapeutic agent for liver dysfunction.

BACKGROUND ART

In the field of regenerative medicine, the use of mesenchymal stem cells for treating tissues in the human body has been attracting attention.

Mesenchymal stem cells are contained in bone marrow aspirates, umbilical cord blood, peripheral blood, and the like, and are cells having a multipotency capable of differentiating into various types of cells, such as those in bones, cartilages, fat, heart, nerves, and liver. However, mesenchymal stem cells comprise, for example, about 0.05% of the total cells in bone marrow aspirates, while it is necessary to collect a large amount for direct clinical use. Such a direct clinical use is a heavy burden for the living body and, therefore, use of cells obtained by subculturing mesenchymal stem cells collected from living tissue is desirable.

Proliferation of mesenchymal stem cells to a desired amount by primary culturing and subculturing of a collected bone marrow aspirate is conventionally already known (Patent Literature 1).

PRIOR ART DOCUMENTS

Patent Literature

Patent Literature 1
Japanese Patent Laid-Open No. 2011-67175.

SUMMARY OF INVENTION

Problems to be Solved by the Invention

In Patent Literature 1, a simple subculture for culturing mesenchymal stem cells to a predetermined amount is disclosed, but the activity (quality) of the cultured mesenchymal stem cells is not considered.

As described in Patent Literature 1, the activity of mesenchymal stem cells is known to decrease (aging) as their culturing continues. Moreover, subculturing involves the repetition of dividing mesenchymal stem cells cultured in a container into plural containers and culturing them; and, therefore, culturing conditions vary among the containers.

Accordingly, final collections of cultured mesenchymal stem cells include aged and dead cells and there is a possibility of failing to acquire a sufficient quality and amount required for clinical use.

In view of such circumstances, the present invention provides a method for evaluating the activity level of cultured mesenchymal stem cells, as well as a method for culturing mesenchymal stem cells using the evaluation method, a method for producing a therapeutic agent for liver dysfunction, and a therapeutic agent for liver dysfunction.

Means for Solving the Problems

Accordingly, the present invention relates to a method for evaluating the activity of mesenchymal stem cells, characterized by comprising a collection step for collecting a subject fluid containing mesenchymal stem cells such as a bone marrow aspirate, umbilical cord blood, or peripheral blood; an isolation step for isolating mesenchymal stem cells from the collected subject fluid; an assay step for assaying the amount of adenylate kinase 4 in the isolated mesenchymal stem cells; and a determination step for determining the activity level of the mesenchymal stem cells from the assayed amount of adenylate kinase 4.

The invention also relates to a method for culturing mesenchymal stem cells, characterized by comprising a collection step of collecting a subject fluid containing mesenchymal stem cells such as a bone marrow aspirate, umbilical cord blood, or peripheral blood; an isolation step of isolating mesenchymal stem cells from the collected subject fluid; a culturing step of culturing the isolated mesenchymal stem cells; a sampling step of sampling a part of cultured mesenchymal stem cells; an assay step of assaying the amount of adenylate kinase 4 in the sampled mesenchymal stem cells; and a determination step of determining the activity level of the mesenchymal stem cells from the assayed amount of adenylate kinase 4.

The invention also relates to a method for producing a therapeutic agent for liver dysfunction, characterized by comprising a collection step of collecting a bone marrow aspirate; an isolation step of isolating a fluid containing mesenchymal stem cells from the collected bone marrow aspirate; a culturing step of culturing mesenchymal stem cells in the isolated fluid; a sampling step of sampling cultured mesenchymal stem cells; an assay step of assaying the amount of adenylate kinase 4 in the sampled mesenchymal stem cells; and a determination step of determining the activity level of the mesenchymal stem cells from the assayed amount of adenylate kinase 4.

The invention also relates to a therapeutic agent for liver dysfunction, characterized in that the agent is produced by steps comprising: an isolation step of isolating a fluid; a culturing step of culturing mesenchymal stem cells in the isolated fluid; a sampling step of sampling the cultured mesenchymal stem cells; an assay step of assaying the amount of adenylate kinase 4 in the sampled mesenchymal stem cells; and a determination step of determining the activity level of the mesenchymal stem cells from the assayed amount of adenylate kinase 4.

Advantageous Effects of Invention

In the invention, the activity level of the mesenchymal stem cells can be evaluated from the assayed amount of adenylate kinase 4; for instance, if the activity level of the mesenchymal stem cells is high, the mesenchymal stem cells can be evaluated as ideal for use as a therapeutic agent.

Conversely, if the mitochondrial activity level of the mesenchymal stem cells is high, then the cells are aged in the view point of aging and the cells can be evaluated as not preferably being used for subculturing, while if the mitochondrial activity of the mesenchymal stem cells is low and aging does not proceed, the mesenchymal stem cells can be evaluated as suitable for subculturing.

MODE FOR CARRYING OUT THE INVENTION

Figure 1:
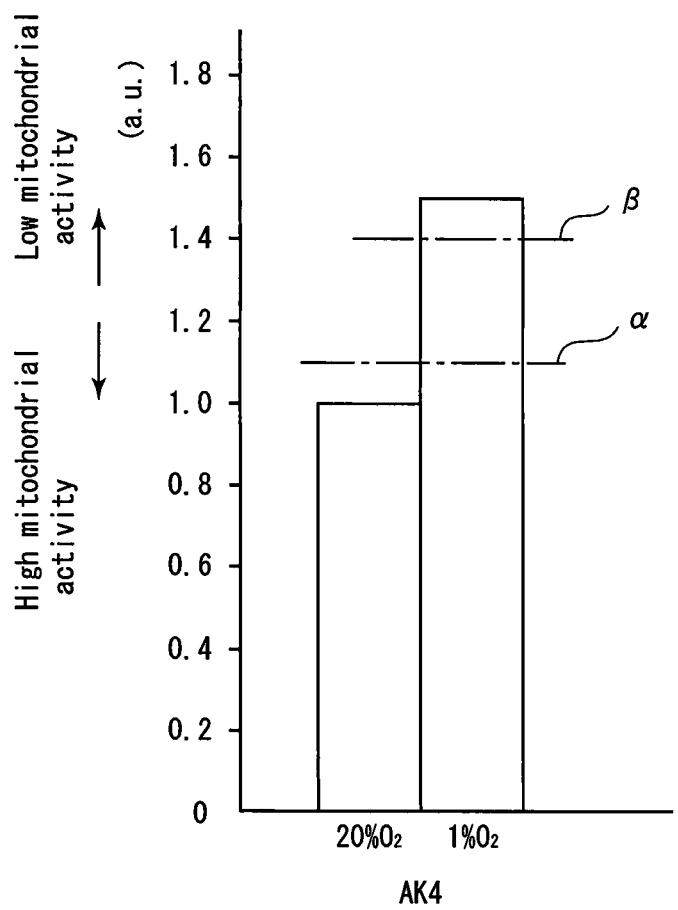
FIG. 1 is a figure of experimental results illustrating the results of assaying the amount of adenylate kinase 4 when the mesenchymal stem cells were cultured under conditions at 1% oxygen and when they were cultured under conditions at 20% oxygen.

The present invention is characterized by assaying an amount of adenylate kinase 4 in mesenchymal stem cells and evaluating the activity level of the mesenchymal stem cells by the assayed amount of adenylate kinase 4.

Adenylate kinase plays an important role in the maintenance of homeostasis of intracellular adenine nucleotides required for the living body to exhibit functions such as proliferation, differentiation, exercise, and metabolism normally and is an enzyme catalyzing the following reversible reaction.

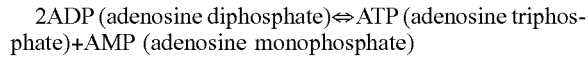

2ADP (adenosine diphosphate)⇔ATP (adenosine triphosphate)+AMP (adenosine monophosphate)

Adenylate kinase has 4 isozymes: adenylate kinase 1 (AK1) located in cytoplasm, adenylate kinase 2 (AK2) located in the mitochondrial inner membrane and adenylate kinase 3 (AK3) and adenylate kinase 4 (AK4) located in the mitochondrial matrix.

The functions of AK1, AK2, and AK3 have been gradually revealed in recent years but the function of AK4 is not well understood.

The present inventors conducted various experiments on AK4 and found as a result that the activity level of mesenchymal stem cells can be evaluated from the amount of AK4, thereby completing the present invention.

FIG. 1 illustrates the results of assaying the amount (expression) of AK4 by microarray analysis when human mesenchymal stem cells collected from a bone marrow aspirate were cultured under conditions at 1% oxygen and when they were cultured under conditions at 20% oxygen.

As apparent from the figure, while the amount of AK4 in the mesenchymal stem cells cultured under the conditions at 20% oxygen was 1 (in arbitrary unit, hereinafter abbreviated as a. u.), the amount of AK4 in mesenchymal stem cells cultured under the conditions at 1% oxygen was 1.50 (in a.u.). It is well known that the mesenchymal stem cells have a higher mitochondrial activity under the conditions at 20% oxygen than at under the conditions at 1% oxygen. From this, it can be seen that when the amount of AK4 is high, the mitochondrial activity is low and the activity of mesenchymal stem cells (stem cell activity) is high and that when the amount of AK4 is low, the mitochondrial activity is high and the activity of mesenchymal stem cells (stem cell activity) is low.

The aforementioned amount of AK4 can be evaluated by western blotting. It can be also estimated by a commercially available flux analyzer (for example, XFe96 from Seahorse Bioscience Inc.).

In the present invention, the activity level of the mesenchymal stem cells can be evaluated from the assayed amount of AK4 and, therefore, this evaluation can be used as follows.

First, the mesenchymal stem cells having a higher activity have a higher effect as a therapeutic agent and, therefore, the mesenchymal stem cells having a high activity can be selected and used as a therapeutic agent, or can be used in a method for producing such a therapeutic agent.

Specifically, when a bone marrow aspirate is collected from a person with liver dysfunction, if the amount of AK4 assayed by steps comprising: a separation step of separating a fluid (the mononuclear cell component) from the bone marrow aspirate; a culturing step of culturing mesenchymal stem cells in the isolated fluid; a sampling step of sampling cultured mesenchymal stem cells; an assay step of assaying the amount of AK4 in the sampled mesenchymal stem cells; and a determination step of determining the activity level of the mesenchymal stem cells from the assayed amount of AK4, is high, then the activity level of the mesenchymal stem cells is high and the mesenchymal stem cells can be used as a therapeutic agent for liver dysfunction. Moreover, the aforementioned steps can be used as a method for producing a therapeutic agent for liver dysfunction.

Second, when subculturing is necessary for proliferating collected mesenchymal stem cells to a predetermined amount, the mesenchymal stem cells not having too much expression of AK4 are preferably subcultured, since too much expression of AK4 in the cultured mesenchymal stem cells results in inhibition of proliferative capacity when used as a therapeutic agent, Specifically, when a subject fluid containing mesenchymal stem cells such as a bone marrow aspirate, umbilical cord blood, or peripheral blood is collected, if the amount of AK4 assayed by a collection step of collecting the subject fluid; an isolation step of isolating mesenchymal stem cells from the collected subject fluid; a culturing step of culturing the isolated mesenchymal stem cells; a sampling step of sampling a part of the cultured mesenchymal stem cells; an assay step of assaying the amount of AK4 in the sampled mesenchymal stem cells; and a determination step of determining the activity level of the mesenchymal stem cells from the assayed amount of AK4, is low, then the mitochondrial activity level in the mesenchymal stem cells is high and they are not used for subculturing, while the mesenchymal stem cells having a high amount of AK4 have a low mitochondrial activity level and, therefore, can be used for subculturing.

In this case, when subculturing involving dividing mesenchymal stem cells cultured in a container into plural containers and culturing is repeated a required number of times, plural mesenchymal stem cells having high and uniform amounts of AK4 may be selected to keep the culture conditions in the containers as uniform and in good qualities as possible. This makes it possible to obtain uniform and good qualities of mesenchymal stem cells in an amount sufficient for clinical use.

Third, when subculturing is necessary for proliferating the collected mesenchymal stem cells to a predetermined amount, if the number of times of the subculturing can be predicted beforehand, then the amount of AK4 at the time of the start of each subculturing can be selected so that the activity of the mesenchymal stem cells becomes high enough to obtain a good effect as a therapeutic agent when the last subculturing is finished.

Accordingly, when subculturing, it is not necessary to select mesenchymal stem cells having the highest amount of AK4, but it is possible to select mesenchymal stem cells having the most suitable amount of AK4 in consideration of the number of times of subculturing between the mesenchymal stem cells having the lowest amount of AK4, in which the mesenchymal stem cells are aged, and the mesenchymal stem cells having the highest amount of AK4.

The amount of AK4 when subculturing may be determined based on the period of cell culturing and the number of times of subculturing so that the cells will have a high or low activity at a certain time point.

Figure 2:
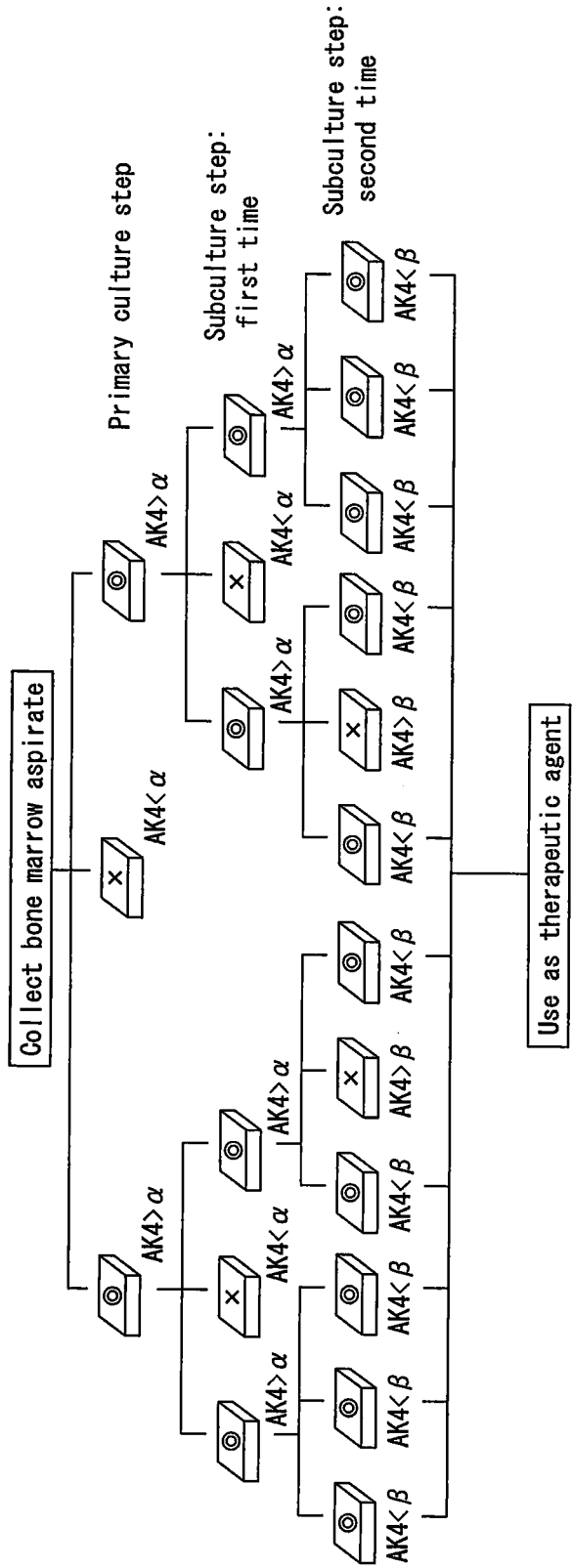
FIG. 2 is an illustration that illustrates the relation between the amount of adenylate kinase 4 and the culturing step.

Examples (Primary Culture Step)
(1) To mesenchymal stem cells prepared from myeloblasts, a culture solution is added to a total volume of 30 mL, and 10 mL aliquots are transferred into 3 flasks to start culturing in an incubator (culturing step: see FIG. 2).

In this example, the collected mesenchymal stem cells are divided into 3 groups in 3 flasks in different culture conditions and cultured.
(2) The total volume of the medium is changed every 2-3 days (medium change step).
(Subculturing Step: First Time)
(1) 10,000 mesenchymal stem cells are each sampled from the 3 flasks in the primary culturing step (sampling step).
(2) The amount of intracellular AK4 in each sample is assayed (assay step). The amount of AK4 can be estimated by a flux analyzer as described above. Alternatively, the amount can be precisely assayed by western blotting or the expression analysis of mRNA.
(3) Whether the assayed amount of AK4 is equal to or higher than a predetermined threshold $\alpha$ or not is verified (determination step). As this threshold $\alpha$, for example, the value 1.1 a.u. in FIG. 1 can be adopted. If the amount is equal to or higher than the value, then the mitochondrial activity of the primary cultured mesenchymal stem cells is low and aging does not proceed, and the mesenchymal stem cells can be evaluated as suitable for subculturing.

On the other hand, if the assayed amount of AK4 is lower than the predetermined threshold $\alpha$, then it is estimated that the mitochondrial activity level in the mesenchymal stem cells is high and these cells are not used for subculturing.

In FIG. 2, since the amounts of AK4 in the right and left mesenchymal stem cells among the mesenchymal stem cells divided into 3 flasks are equal to or higher than the threshold $\alpha$, these cells are subcultured (see the mark @). Since the amount of AK4 in the mesenchymal stem cells in the central flask is lower than the threshold $\alpha$, these cells are not subcultured (see the mark ×). Meanwhile, the mesenchymal stem cells in the central flask, which are not subcultured, are not abandoned at this time point, but culturing is continued in an incubator.

On the other hand, the right and left mesenchymal stem cells, which are determined to be subcultured, are transferred into 3 flasks each and cultured in an incubator. In this example, the primary cultured mesenchymal stem cells are divided into 6 groups and the first subculturing is performed.
(Subculturing Step: Second Time)
(1) 10,000 mesenchymal stem cells are each sampled from the aforementioned 6 flasks (sampling step).
(2) The amount of AK4 in the sampled cells is assayed (assay step).
(3) If the assayed amount of AK4 is equal to or higher than the threshold $\alpha$, the cells in the sampled flask are further transferred into 3 flasks and the second subculturing is performed in an incubator.

In the case illustrated in FIG. 2, since the amounts of AK4 in the mesenchymal stem cells in the 4 groups with the mark @ among the mesenchymal stem cells divided into 6 groups in the first subculturing are equal to or higher than the threshold $\alpha$, the second subculturing is performed for these 4 groups. Since the amounts of AK4 in the mesenchymal stem cells in the 2 remaining groups with the mark × are less than the threshold $\alpha$, these cells are not subcultured. Meanwhile, the mesenchymal stem cells in the 2 groups, which are not subcultured, are not abandoned at this time point, but culturing is continued in an incubator.

On the other hand, the mesenchymal stem cells in the 4 groups, which are determined to be subcultured, the mesenchymal stem cells in each group are transferred into 3 flasks each and cultured in an incubator. The mesenchymal stem cells are divided into 12 groups in total and the second subculturing is performed.
(Cell Suspension Preparation Step)
(1) 10,000 mesenchymal stem cells are each sampled from the aforementioned 12 flasks. Moreover, 10,000 mesenchymal stem cells are each sampled as well from the other 3 flasks, which are not subcultured.
(2) The amount of AK4 in the sampled cells is assayed.
(3) If the assayed amount of AK4 is equal to or lower than the predetermined threshold $\beta$, for example, equal to or lower than the threshold $\beta$=1.4 a.u., then these mesenchymal stem cells are subjected to the separation of cells by washing the flask and a total 200 mL of a cell suspension can be prepared by adding agents and a physiological saline and used as a therapeutic agent.

On the other hand, if the assayed amount of AK4 is higher than the threshold $\beta$, then the mitochondrial activity level of the mesenchymal stem cells is low and the proliferative capacity decreases. Accordingly, these mesenchymal stem cells are unlikely to be effective when used as a therapeutic agent and they are abandoned. However, depending on the conditions, for example, when the total amount of the therapeutic agent is low, even mesenchymal stem cells having a low mitochondrial activity level are desirable to be used as a therapeutic agent rather than to be abandoned.

Although it is desirable to proliferate cells by subculturing to reduce the patient burden, if a sufficient amount of mesenchymal stem cells can be collected, then the amount of AK4 in the mesenchymal stem cells is assayed after the primary cell culturing is performed and cells having an assayed amount of AK4 that is equal to or lower than the threshold $\beta$ can be used as a therapeutic agent without performing subculturing.

Moreover, the numerical values of the aforementioned thresholds $\alpha$ and $\beta$ for the amount of AK4 are examples and may be of course changed or adjusted to the most suitable value as appropriate depending on the required conditions such as the site to be used as a therapeutic agent and the necessary number of times of subculturing.

The invention claimed is:
1. A method of culturing mesenchymal stem cells comprising the steps of:
 isolating mesenchymal stem cells from a subject fluid containing mesenchymal stem cells;
 culturing the isolated mesenchymal stem cells;
 sampling a part of the cultured mesenchymal stem cells;
 assaying the amount of adenylate kinase 4 in the sampled mesenchymal stem cells; and
 subculturing the assayed sampled mesenchymal stem cells if the assayed amount of adenylate kinase 4 is equal to or higher than a threshold $\alpha$ which is greater than the assayed expression of adenylate kinase 4 when the mesenchymal stem cells are cultured under conditions at 20% oxygen.

2. The method of claim 1, wherein the subject fluid is a bone marrow aspirate, umbilical cord blood or peripheral blood.

3. The method of claim 1, wherein the culturing step comprises dividing the mesenchymal stem cells into plural groups and culturing the plural groups and the sampling step comprises sampling a part of each of the plural groups of mesenchymal stem cells.

4. The method of claim 1, wherein the sampled group of mesenchymal stem cells is not subcultured in the subculturing step if the assayed amount of adenylate kinase 4 is lower than the threshold $\alpha$.

5. The method of claim 1, wherein the sampled mesenchymal stem cells are used as a therapeutic agent in the subculturing step if the assayed amount of adenylate kinase 4 is equal to or lower than a threshold $\beta$ which is smaller than the assayed expression of adenylate kinase 4 when the mesenchymal stem cells are cultured under conditions at 1% oxygen.

6. The method of claim 1, additionally comprising the steps of:
   sampling a part of the mesenchymal stem cells subcultured in the subculturing step;
   assaying the amount of adenylate kinase 4 in the sampled subcultured mesenchymal stem cells;
   subculturing the sampled subcultured mesenchymal stem cells if the amount of adenylate kinase 4 is equal to or higher than the threshold $\alpha$; and
   repeating these steps at least one time.

7. The method of claim 6, wherein the subculturing step comprises dividing the mesenchymal stem cells into plural groups and subculturing the plural groups.

* * * * *